United States Patent [19]

Tsuchida et al.

[11] Patent Number: 5,531,097
[45] Date of Patent: Jul. 2, 1996

[54] ABSOLUTE HUMIDITY METER

[75] Inventors: Atsuko Tsuchida; Shiro Nakagawa, both of Tokyo, Japan

[73] Assignee: TDK Corporation, Tokyo, Japan

[21] Appl. No.: 385,877

[22] Filed: Feb. 9, 1995

[30] Foreign Application Priority Data

Feb. 9, 1994 [JP] Japan .................... 6-015589
Dec. 14, 1994 [JP] Japan .................... 6-310797

[51] Int. Cl.⁶ .......................... G01W 1/00; G01N 27/12
[52] U.S. Cl. .................. 73/29.02; 73/29.01; 73/335.02; 73/335.03; 324/667; 324/677
[58] Field of Search .................... 73/29.01, 29.02, 73/335.02, 335.03, 29.05; 324/667, 677

[56] References Cited

U.S. PATENT DOCUMENTS

| | | | |
|---|---|---|---|
| 3,719,810 | 3/1973 | Ahlquist et al. | 235/151.3 |
| 3,831,450 | 8/1974 | Schipke et al. | 73/336 |
| 4,379,406 | 4/1983 | Bennewitz et al. | 73/336.5 |
| 4,793,182 | 12/1988 | Djorup | 73/336.5 |
| 5,065,625 | 11/1991 | Nakagawa et al. | 73/336.5 |
| 5,317,274 | 5/1994 | Nakagawa et al. | 324/678 |
| 5,396,796 | 3/1995 | Kotani et al. | 73/431 |

FOREIGN PATENT DOCUMENTS

1141347  6/1989  Japan .................... 73/335.03

Primary Examiner—Hezron E. Williams
Assistant Examiner—J. David Wiggins
Attorney, Agent, or Firm—Oblon, Spivak, McClelland, Maier & Neustadt

[57] ABSTRACT

An absolute humidity meter in which a humidity sensor changes an electrical impedance thereof-exponentially with respect to the relative humidity. A z-f converting circuit (impedance to frequency) generates a pulse signal corresponding to the impedance. A time constant control differentiating circuit has an impedance of a voltage control variable impedance element changed exponentially by a control voltage, and outputs a differentiated signal obtained by differentiating the pulse signal. A waveform shaping circuit outputs a pulse signal train obtained by binary-valued the differentiated signal. An integrating circuit causes a first integrating circuit to obtain the control voltage by integrating the pulse signal train and a second integrating circuit to obtain an output voltage of a relative humidity signal by integrating the pulse signal train, and obtains an absolute humidity signal by causing at least one of these integrating circuit to control the control voltage or the output voltage with increasing temperature.

16 Claims, 8 Drawing Sheets

ABSOLUTE HUMIDITY METER

BACKGROUND OF THE INVENTION

The invention relates to absolute humidity meters.

Known as an absolute humidity meter adapted for use in various types of electronic devices such as copying machines and printers is one based on the heat dissipation coefficient of a thermistor. Such conventional art is disclosed in, e.g., Examined Japanese Patent Publication (Kokoku) Hei-4-50529, a special number "Temperature/Humidity Meter Handbook" of a periodical "Transistor Technology" published in Jan. 1, 1985 (see "How absolute humidity meters are used" in Chapter 2), and the like.

Such an absolute humidity meter utilizes the negative temperature coefficient of resistance of a thermistor, and includes two thermistors. One of the thermistors is arranged within an object to be measured, and the other within a closed dry air environment. The two thermistors are connected in series with each other, and self-heated. A temperature difference between the two thermistors caused by the heat of one of the thermistors being dissipated from the object to be measured is detected as a difference in resistance, so that an absolute humidity signal is obtained from a change in voltage corresponding to the difference in resistance. That is, the heat dissipation coefficient of the one thermistor changes with absolute humidity, and the other thermistor has a fixed heat dissipation coefficient that is in accordance with the dry air, so that a difference in resistance between both thermistors can be detected as the absolute humidity. The other thermistor provides temperature compensation.

However, the aforementioned conventional absolute humidity meter has not addressed the following problems.

Since two thermistors are used, the heat dissipation coefficients are changed by turbulences present in the object to be measured, which in turn impairs measurement accuracy.

Variations in the heat dissipation coefficients of the two thermistors, location temperature differences, and the like impair measurement accuracy.

The heat dissipation coefficients of the two thermistors must be made equal to each other with changing ambient temperatures. However, to select thermistors whose heat dissipation coefficients are equal to each other is difficult. To eliminate the difference between the heat dissipation coefficients, it is necessary to provide a temperature compensation circuit, which in turn complicates the circuit configuration.

Small analog signals must be processed, which makes the circuits necessary for achieving such temperature compensation function not only complicated but also expensive.

SUMMARY OF THE INVENTION

Accordingly, an object of the invention is to provide an absolute humidity meter that is not based on the heat dissipation coefficient of a thermistor.

Another object of the invention is to provide an absolute humidity meter that is less affected by variations between a plurality of detecting elements, location temperature differences, and the like while using only one detecting element.

Still another object of the invention is to provide an absolute humidity meter that can be used also as a relative humidity meter by using a detecting element whose impedance changes with relative humidity.

Still another object of the invention is to provide an absolute humidity meter that is less affected by temperature variations.

Still another object of the invention is to provide an absolute humidity meter that can facilitate signal processing and that can be manufactured inexpensively.

Still another object of the invention is to provide an absolute humidity meter to which a variety of types of humidity sensors can be applied.

To achieve the above objects, the invention is applied to an absolute humidity meter that includes: a humidity sensor; an impedance-frequency converting circuit; a time constant control differentiating circuit; a waveform shaping circuit; and an integrating circuit. The humidity sensor has an impedance thereof changed exponentially with respect to a relative humidity. The impedance-frequency converting circuit generates a pulse signal whose frequency corresponds to the impedance of the humidity sensor. The time constant control differentiating circuit includes a capacitor and a voltage control variable impedance element which are connected in series with each other. The voltage control variable impedance element is constructed of a three-terminal element having main electrodes and a control electrode, changes an impedance thereof exponentially with a voltage applied to the control electrode, and outputs a differentiated signal obtained by differentiating the pulse signal across both terminals of the main electrodes. The waveform shaping circuit receives the differentiated signal and outputs a pulse signal train obtained by binary-valued the differentiated signal by a predetermined voltage. The integrating circuit includes a first integrating circuit and a second integrating circuit, the first integrating circuit integrating the inputted pulse signal train and supplying a voltage obtained by the integration to the control electrode of the voltage control variable impedance element as the control voltage, the second integrating circuit integrating the pulse signal train and outputting a voltage obtained by the integration as a relative humidity signal, the integrating circuit obtaining an absolute humidity signal by causing at least one of the first integrating circuit and the second integrating circuit to control the control voltage or the output voltage of the relative humidity signal with respect to any changes in the temperature of the humidity sensor.

It is preferred that the humidity sensor, the impedance-frequency converting circuit, the time constant control differentiating circuit, the waveform shaping circuit, and the integrating circuit be contained in a single case.

It is preferred that: the first integrating circuit have a resistance dividing circuit and a capacitor; the resistance dividing circuit include a fixed resistor and a variable impedance circuit whose impedance changes with temperature; the capacitor be connected in parallel with either the fixed resistor or the variable impedance circuit; and a terminal voltage of the capacitor become the control voltage. In a preferred embodiment of the first integrating circuit, the variable impedance circuit includes at least one of a negative temperature coefficient (TC) type thermistor, a, diode, a transistor, and a positive TC type thermistor.

It is preferred that: the second integrating circuit have a resistance dividing circuit and a capacitor; the resistance dividing circuit include a fixed resistor and a thermistor; the capacitor be connected in parallel with either the fixed resistor or the thermistor; and a terminal voltage of the capacitor become an output voltage of the absolute humidity signal. In a preferred embodiment of the second integrating circuit, the thermistor is constructed of a negative TC type thermistor or a positive TC type thermistor.

It is preferred that: the voltage control variable impedance element include a transistor; the collector and the emitter of the transistor constitute the main electrodes; and the base thereof constitute the control electrode. In a preferred embodiment of the voltage control variable impedance element, two transistors are included and these two transistors are Darlington-connected.

It is preferred that: the time constant control differentiating circuit include a nonlinear impedance element whose impedance changes exponentially by an applied voltage; the nonlinear impedance element be connected to the main electrode opposite to the main electrode to which the capacitor is connected; and the differentiated signal be outputted across both terminals of the voltage control variable impedance element and the nonlinear impedance element connected in series with each other. In a preferred embodiment of the time constant control differentiating circuit, the nonlinear impedance element is constructed of a diode, an anode of the diode being connected to the main electrode opposite to the main electrode to which the capacitor is connected.

It is further preferred that: the time constant control differentiating circuit have an impedance adjusting circuit; and the impedance adjusting circuit be connected in parallel with the nonlinear impedance element. In a preferred embodiment of the time constant control differentiating circuit, the impedance adjusting circuit includes at least one of a capacitor, a resistor, and a diode.

It is still further preferred that: the time constant control differentiating circuit have a control voltage adjusting circuit; and the control voltage adjusting circuit bias the nonlinear impedance element in accordance with a voltage obtained by the integration at the first integrating circuit. In a preferred embodiment of the time constant control differentiating circuit, the control voltage adjusting circuit includes a transistor and a fixed resistor. The collector of the transistor is connected to the capacitor of the first integrating circuit and the emitter thereof is connected to the nonlinear impedance element. The fixed resistor is connected to the emitter and the base of the transistor.

The humidity sensor changes an impedance thereof exponentially with respect to the relative humidity, and the impedance-frequency converting circuit generates a pulse signal whose frequency corresponds to the impedance of the humidity sensor. Therefore, a pulse signal whose frequency changes exponentially with respect to the relative humidity can be obtained from the impedance-frequency converting circuit.

The time constant control differentiating circuit has the capacitor and the voltage control variable impedance element connected in series with each other; the voltage control variable impedance element is constructed of a three-terminal element having main electrodes and a control electrode; the impedance of the voltage control variable impedance element changes exponentially with a voltage applied to the control electrode; and a differentiated signal obtained by differentiating the pulse signal is outputted across both terminals of the main electrodes. Therefore, a differentiated signal whose time constant changes exponentially with changing impedance of the voltage control variable impedance element can be obtained.

The waveform shaping circuit receives the differentiated signal whose time constant changes exponentially and outputs a pulse signal train obtained by binary-valued the differentiated signal by a predetermined voltage. Therefore, a pulse signal train having a pulse width that is obtained by compressing the pulse width of the pulse signal logarithmically with respect to the frequency can be obtained from the waveform shaping circuit. As a result, a linearized relative humidity signal can be obtained by integrating the pulse signal train.

In the integrating circuit, the first integrating circuit integrates the inputted pulse signal train and supplies a voltage obtained by the integration to the control electrode of the voltage control variable impedance element as the control voltage. Therefore, when the pulse width of the pulse signal train is increased to increase the control voltage, the impedance of the voltage control variable impedance element is decreased. As a result, the pulse width of the pulse signal train obtained from the waveform shaping circuit is decreased, thereby checking the control voltage from increasing. Conversely, when the pulse width of the pulse signal train is decreased to decrease the control voltage, the impedance of the voltage control variable impedance element is increased. As a result, the pulse width of the pulse signal train obtained from the waveform shaping circuit is increased, thereby checking the control voltage from decreasing. That is, the first integrating circuit degenerates the time constant control differentiating circuit, which in turn stabilizes the pulse signal train. As a result of this operation, the linearity of the relative humidity signal can be improved.

In the integrating circuit, the second integrating circuit integrates the pulse signal train and outputs a voltage obtained by the integration as a relative humidity signal. Therefore, a linearized relative humidity signal can be obtained from the second integrating circuit.

An absolute humidity signal is obtained by causing at least one of the first integrating circuit and the second integrating circuit to control the control voltage or the output voltage of the relative humidity signal with changes in the temperature of the humidity sensor. Therefore, e.g., when the first integrating circuit decreases the control voltage with increasing temperature, the impedance of the voltage control variable impedance element is increased with increasing temperature, which in turn increases the pulse width of the pulse signal train and thereby increases the output voltage of the relative humidity signal. The second integrating circuit linearly increases the output voltage of the relative humidity signal with increasing temperature. If the output voltage of the relative humidity is replaced by the absolute humidity, the amount of saturated moisture is increased with increasing temperature, it is necessary to increase the output voltage of the relative humidity with increasing temperature. Therefore, when the output voltage of a highly linear relative humidity signal is appropriately increased with increasing temperature, a highly linear absolute humidity signal can be obtained. In case of decreasing temperature, the first integrating circuit increases the control voltage, and the second integrating circuit decreases the output voltage of the relative humidity signal.

Since there is no need for the humidity sensor to be self-heated as described above, an absolute humidity meter that dose not utilize the heat dissipation coefficient can be obtained. As a result, the absolute humidity meter becomes highly resistant to disturbance.

Further, since the humidity sensor can be constructed of a single detecting element, an absolute humidity meter that is less affected by variations between a plurality of detecting elements and location temperature differences can be obtained. In addition, no humidity sensor for temperature compensation is necessary, so that the selecting of detecting elements to match the characteristics thereof can be dispensed with, which in turn facilitates the manufacture of absolute humidity meters.

Still further, since the integrating circuit obtains the absolute humidity signal by increasing the output voltage of the relative humidity signal with increasing temperature, an absolute humidity meter that can be used also as a relative humidity meter can be obtained.

Still further, since no temperature-compensating humidity sensor is required, an absolute humidity meter that is less affected by temperature variations can be obtained.

Still further, since the humidity sensor changes an impedance thereof exponentially with respect to the relative humidity, and the impedance-frequency converting circuit generates a pulse signal whose frequency corresponds to the impedance of the humidity sensor, the frequency of the pulse signal changes to a large extent. In addition, the signals are processed digitally, which in turn facilitates signal processing and therefore allows an inexpensive absolute humidity meter to be obtained.

In the embodiment in which the humidity sensor, the impedance-frequency converting circuit, the time constant control differentiating circuit, the waveform shaping circuit, and the integrating circuit are contained in a single case, an absolute humidity meter that is not only downsized but also less affected by temperature variations because the humidity sensor and the integrating circuit are disposed under the same temperature conditions can be obtained.

In the embodiment in which the resistance dividing circuit of the first integrating circuit includes a fixed resistor and a variable impedance circuit whose impedance changes with temperature and the capacitor is connected in parallel with either the fixed resistor or the variable impedance circuit so that a terminal voltage of the capacitor becomes the control voltage, the impedance of the variable impedance circuit increases or decreases with increasing temperature and the control voltage is decreased in association therewith. As a result, an absolute humidity signal can be obtained through the second integrating circuit by increasing the output voltage of the relative humidity signal with increasing temperature.

In the embodiment in which the variable impedance circuit includes at least one of a negative TC type thermistor, a diode, a transistor and the negative TC type thermistor and the like are connected in parallel with the capacitor, the resistance of the negative TC type thermistor and the impedance of the diode or the transistor in operation are decreased with increasing temperature, which in turn decreases the divided voltage of the negative TC type thermistor and the like and thereby decreases the control voltage.

In the embodiment in which the resistance dividing circuit of the second integrating circuit includes a fixed resistor and a thermistor and the capacitor is connected in parallel with either the fixed resistor or the thermistor, so that a terminal voltage of the capacitor becomes an output voltage of the absolute humidity signal, the resistance of the thermistor is increased or decreased with increasing temperature. As a result, the output voltage of the relative humidity signal is increased to thereby allow an absolute humidity signal to be obtained across both terminals of the capacitor.

In the embodiment in which the thermistor of the resistance dividing circuit is constructed of a negative TC type thermistor and the capacitor is connected in parallel with the fixed resistor, the divided voltage of the fixed resistor is increased with increasing temperature, which in turn increases the output voltage of the relative humidity signal.

In the embodiment in which the voltage control variable impedance element includes two transistors; the two transistors are Darlington-connected; the collector and the emitter of the transistor constitute the main electrodes; and the base thereof constitutes the control electrode, the impedance of the voltage control variable impedance element changes to a large extent even with small changes in the control voltage. As a result, humidity sensors whose resistance changing rate is small can be used, which in turn provides an absolute humidity meter to which a wide variety of humidity sensors can be applied.

In the embodiment in which the time constant control differentiating circuit includes a nonlinear impedance element whose impedance changes exponentially by an applied voltage; the nonlinear impedance element is connected to the main electrode opposite to the main electrode to which the capacitor is connected; and the differentiated signal is outputted across both terminals of the voltage control variable impedance element and the nonlinear impedance element connected in series with each other, the differentiated signal whose time constant changes exponentially with changing impedance of the voltage control variable impedance element and the nonlinear impedance element can be obtained. Thus the nonlinear impedance element supplements linearity that was short when the conventional voltage control variable impedance element corrected the nonlinearity of the humidity sensor. As result of this operation, the linearity of the output voltage of the relative humidity signal is improved, which in turn allows the linearity of the output voltage of the absolute humidity signal to be also further improved.

In the embodiment in which the voltage control variable impedance element of the time constant control differentiating circuit is constructed of a transistor; the nonlinear impedance element is constructed of a diode; an anode of the diode is connected to the emitter of the transistor; the capacitor is connected to the collector; and the control voltage is supplied to the base of the transistor, the control voltage degenerates the voltage control variable impedance element and the nonlinear impedance element, which in turn improves the linearity of the relative humidity signal.

In the embodiment in which the impedance adjusting circuit of the time constant control differentiating circuit is connected in parallel with the nonlinear impedance element, the impedance of the nonlinear impedance element can be adjusted finely. As a result of this operation, the linearity of the relative humidity signal can further be improved.

In the embodiment in which the time constant control differentiating circuit has a control voltage adjusting circuit; the control voltage adjusting circuit biases the nonlinear impedance element in accordance with a voltage obtained by the integration at the first integrating circuit, the potential of the nonlinear impedance element, i.e., the potential of the main electrode of the voltage control variable impedance element which is opposite to the main electrode to which the capacitor is connected is increased, which is substantially equivalent to a decrease in the divided voltage when the resistance dividing circuit is arranged in the first integrating circuit. Therefore, a wide adjustment range for a variety of types of humidity sensors can be provided.

In the embodiment in which the control voltage adjusting circuit includes a transistor and a fixed resistor; the collector of the transistor is connected to the capacitor of the first integrating circuit; the emitter thereof is connected to the nonlinear impedance element; and the fixed resistor is connected to the emitter and the base of the transistor, the nonlinear impedance element is biased by the current flowing through the transistor in accordance with the voltage obtained by integration at the first integrating circuit, which in turn increases the potential of the nonlinear impedance element.

DETAILED DESCRIPTION OF THE PREFERRED EMBODIMENTS

Figure 1:
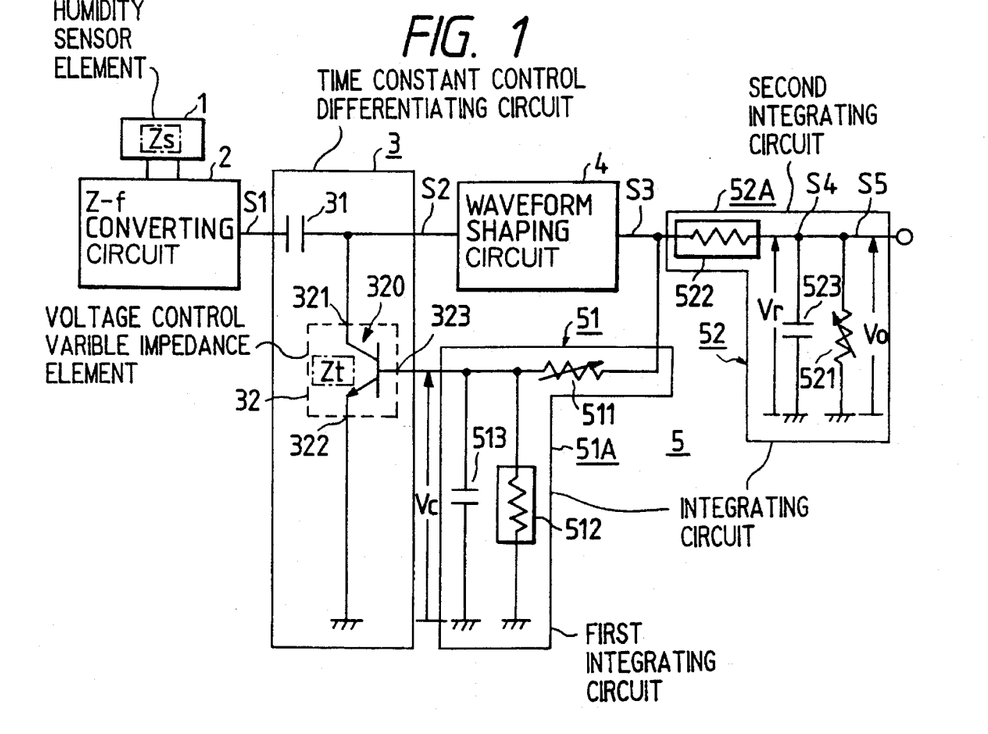
FIG. 1 is a block diagram showing an absolute humidity meter, which is an embodiment of the invention.

FIG. 1 is a block diagram showing a configuration of a humidity meter of the invention. In FIG. 1, reference numeral 1 denotes a humidity sensor; 2, an impedance-frequency converting circuit (hereinafter referred to as "z-f converting circuit"); 3, a time constant control differentiating circuit; 4, a waveform shaping circuit; and 5, an integrating circuit.

Figure 2:
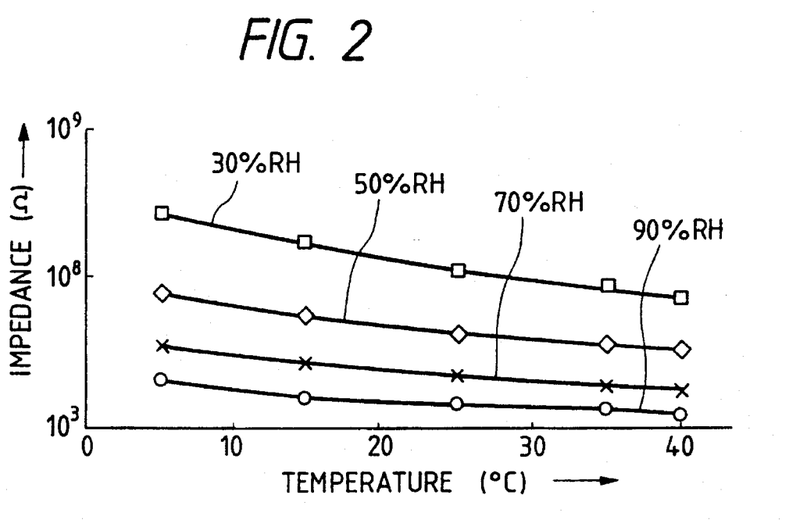
FIG. 2 is a diagram showing changes in the impedance of a humidity sensor.

FIG. 2 is a diagram showing changes in the impedance of the humidity sensor. In FIG. 2 the abscissa indicates the ambient temperature and the ordinate indicates the impedance. FIG. 2 shows changes in the impedance of the humidity sensor when the relative humidity is changed in the range from 30% to 90 % at ambient temperatures of 5°, 15°, 25°, 35°, and 40° C. As shown in FIG. 2, the humidity sensor 1 changes an impedance Zs thereof exponentially with respect to the relative humidity. The humidity sensor 1 according to this embodiment is made of a high molecular material, and exhibits low impedance at high humidity and high impedance at low humidity. Specifically, the impedance of the humidity sensor 1 ranges from $10^4$ to $10^7$ [Ω].

The z-f converting circuit 2 generates a pulse signal S1 whose frequency corresponds to the impedance Zs of the humidity sensor 1. When the impedance Zs is low, the frequency becomes high, whereas when the impedance Zs is high, the frequency becomes low.

The time constant control differentiating circuit 3 includes a capacitor 31 and a voltage control variable impedance element 32. The capacitor 31 is connected in series with the voltage control variable impedance element 32. The voltage control variable impedance element 32 is constructed of a three-terminal element having main electrodes 321, 322, and a control electrode 323, and changes an impedance Zt thereof exponentially in accordance with a control voltage Vc applied to the control electrode 323. The time constant control differentiating circuit 3 outputs a differentiated signal S2, which is a signal obtained by differentiating the pulse signal S1, across both terminals of the main electrodes 321, 322 of the voltage control variable impedance element 32. The voltage control variable impedance element 32 is generally constructed of a transistor 320, with the collector and the emitter of the transistor 320 constituting the main electrodes 321, 322 and the base thereof constituting the control electrode 323.

The waveform shaping circuit 4 receives the differentiated signal S2, and outputs a pulse signal train S3 obtained by binary-valued the differentiated signal S2 by a predetermined voltage.

The integrating circuit 5 includes a first integrating circuit 51 and a second integrating circuit 52. The first integrating circuit 51 integrates the inputted pulse signal train S3, and supplies a voltage obtained by the integration to the control electrode 323 of the voltage control variable impedance element 32 as the control voltage Vc. The second integrating circuit 52 integrates the pulse signal train S3, and outputs a voltage obtained by the integration as a relative humidity signal S4 indicative of the relative humidity at a certain temperature. The integrating circuit 5 produces an absolute humidity signal S5 by causing at least one of the first integrating circuit 51 and the second integrating circuit 52 to control the control voltage Vc or the output voltage Vr of the relative humidity signal S4 with increasing of temperature. Specifically, the first integrating circuit 51 produces the absolute humidity signal S5 by decreasing the control voltage Vc with increasing temperature, thereby making the pulse width of the pulse signal train S3 larger than the pulse width of the relative humidity meter, and thereby increasing the output voltage Vr of the relative humidity signal S4. The second integrating circuit 52 produces the absolute humidity signal S5 by causing a thermistor 522 and a capacitor 523 to integrate the pulse signal train S3 to produce the relative humidity signal S4, and causing the thermistor 522 and a fixed resistor 521 to increase the output voltage Vr of the relative humidity signal S4 with increasing temperature by a resistance dividing ratio. In case of decreasing temperature, the first integrating circuit 51 increases the control voltage Vc and the second integrating circuit 52 drops the output voltage Vr of the relative humidity signal S4 indicative of the relative humidity at a certain temperature.

Since the humidity sensor 1 changes an impedance Zs thereof exponentially with respect to the relative humidity and the z-f converting circuit 2 generates the pulse signal S1 whose frequency corresponds to the impedance Zs of the humidity sensor 1 as described above, the pulse signal S1 whose frequency changes exponentially with respect to the relative humidity can be obtained from the z-f converting circuit 2.

The time constant control differentiating circuit 3 is designed so that: the capacitor 31 is connected in series with the voltage control variable impedance element 32; the voltage control variable impedance element 32 is constructed of the three-terminal element having the main electrodes 321, 322 and the control electrode 323; the impedance Zt changes exponentially with the control voltage Vc applied to the control electrode 323; and the differentiated signal S2 obtained by differentiating the pulse signal S1 is outputted across both terminals of the main electrodes 321, 322. Therefore, the differentiated signal S2 whose time constant changes with changing impedance of the voltage control variable impedance element 32, and hence whose time constant changes exponentially can be obtained.

The waveform shaping circuit 4 is designed so that: the differentiated signal S2 whose time constant changes exponentially is received; and the pulse signal train S3 obtained by binary-valued the differentiated signal S2 by a predetermined voltage is outputted. Therefore, the pulse signal train S3 having a pulse width obtained by compressing the pulse width of the pulse signal S1 logarithmically with respect to the frequency can be obtained from the waveform shaping circuit 4. As a result, a linearized relative humidity signal can be obtained by integrating the pulse signal train S3.

The first integrating circuit 51 integrates the inputted pulse signal train S3 and supplies the voltage obtained by the integration to the control electrode 323 of the voltage control variable impedance element 32 as the control voltage Vc. Therefore, when the pulse width of the pulse signal train S3 is increased to increase the control voltage Vc, the first integrating circuit 51 decreases the impedance Zt of the voltage control variable impedance element 32. As a result, the pulse width of the pulse signal train S3 obtained from the waveform shaping circuit 4 is decreased, thereby checking the control voltage Vc from increasing. Conversely, when the pulse width of the pulse signal train S3 is decreased to decrease the control voltage Vc, the first integrating circuit 51 increases the impedance Zt of the voltage control variable impedance element 32. As a result, the pulse width of the pulse signal train S3 obtained from the waveform shaping circuit 4 is increased, thereby checking the control voltage Vc from decreasing. That is, the first integrating circuit 51 degenerates the time constant control differentiating circuit 3, which in turn stabilizes the pulse signal train S3 and hence improves the linearity of the relative humidity signal.

The second integrating circuit 52 integrates the pulse signal train S3 and outputs the voltage Vr obtained by the integration as the humidity signal S4 indicative of the relative humidity at a certain temperature. Therefore, a linearized relative humidity-output voltage characteristic can be obtained from the second integrating circuit 52.

Figure 3:
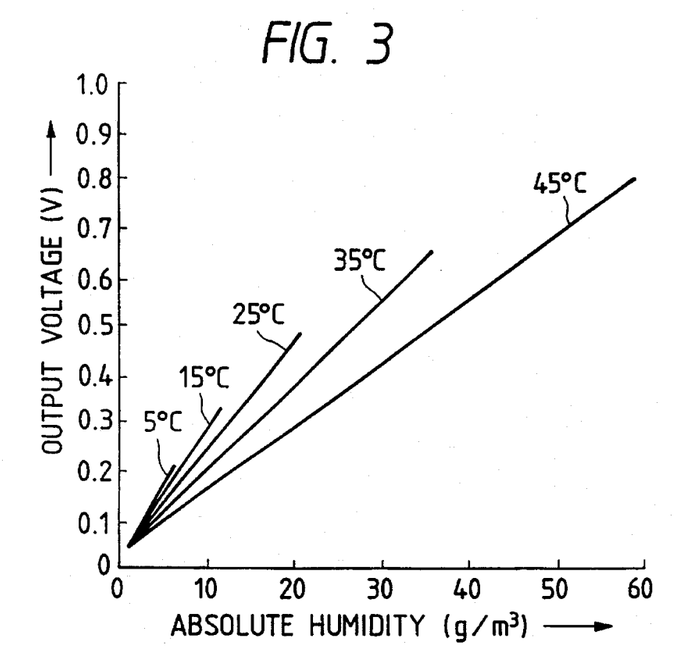
FIG. 3 is a diagram showing the output voltage obtained by a relative humidity meter in terms of a relationship between the absolute humidity and the output voltage.
Figure 4:
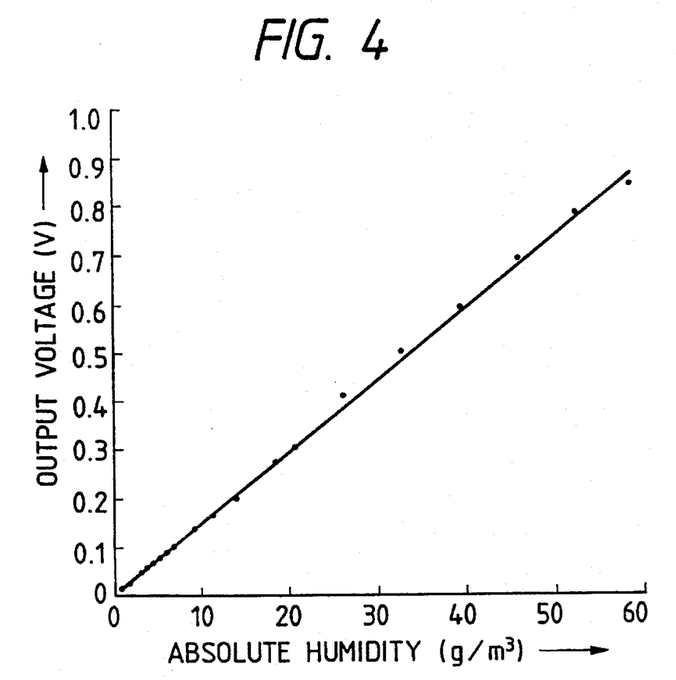
FIG. 4 is a diagram showing a relationship between the absolute humidity and the output voltage of the absolute humidity meter of the invention.

FIGS. 3 and 4 are diagrams illustrative of the concept of the absolute humidity meter of the invention. FIG. 3 shows the output voltage obtained by the relative humidity meter in terms of a relationship between the absolute humidity and the output voltage with the temperature at a measured humidity as a parameter. The relative humidity is changed from 1% to 90%. The abscissa indicates the absolute humidity and the ordinate indicates the output voltage. Since the amount of saturated moisture increases with increasing temperature, the output voltage Vr of the relative humidity signal S4 indicative of the relative humidity at a certain temperature is also adjusted so as to increase with increasing temperature. FIG. 4 is a diagram showing a relationship between the absolute humidity and the output voltage in the case of further increasing the output voltage Vr of the relative humidity signal S4 with increasing temperature.

As shown in FIG. 3, in the case of replacing the output voltage of the relative humidity by the absolute humidity, the amount of saturated moisture increases with increasing temperature. Therefore, it is necessary to increase the output voltage Vr of the relative humidity signal with increasing temperature. While the rate of increase in the output voltage Vr with increasing temperature is insufficient in the example of FIG. 3, if the output voltage Vr of the relative humidity signal S4 is designed to be further increased with increasing temperature, variations in the measured output voltage due to temperature variations are suppressed, thereby allowing the relationship to be linearized as shown in FIG. 4. As a result, a highly linear absolute humidity signal S5 can be obtained by appropriately increasing the output voltage Vr of a highly linear relative humidity signal S4 with increasing temperature.

The integrating circuit 5 obtains the absolute humidity signal S5 by causing at least one of the first integrating circuit 51 and the second integrating circuit 52 to control the control voltage Vc or the output voltage Vr of the relative humidity signal S4 with increasing temperature. Therefore, when, e.g., the first integrating circuit 51 decreases the control voltage Vc with increasing temperature, the impedance Zt of the voltage control variable impedance element 32 increases with increasing temperature, which in turn increases the pulse width of the pulse signal train S3 and hence increases the output voltage Vr of the relative humidity signal S4 indicative of the relative humidity at a certain temperature. The second integrating circuit 52 directly increases the output voltage Vr of the relative humidity signal S4 with increasing temperature. In case of decreasing temperature, the first integrating circuit 51 increases the control voltage Vc and the second integrating circuit 52 decreases the output voltage Vr of the relative humidity signal S4 indicative of the relative humidity at a certain temperature. As a result of this operation, the output voltage Vr of a highly linear relative humidity signal S4 is appropriately increased with increasing temperature, so that a highly linear absolute humidity signal S5 can be obtained.

Since the humidity sensor 1 is not required to be self-heated as described above, an absolute humidity meter not based on heat dissipation coefficient can be obtained. Therefore, the absolute humidity meter is highly resistant to disturbance.

Further, the humidity sensor 1 can be constructed of a single detecting element, an absolute humidity meter that is less affected by variations between a plurality of detecting elements and location temperature differences. In addition, no humidity sensor for temperature compensation is necessary, so that the selecting of detecting elements to match the characteristics thereof can be dispensed with, which in turn facilitates the manufacture of absolute humidity meters.

Still further, the integrating circuit 5 increases the output voltage Vr of the relative humidity signal S4 indicative of the relative humidity at a certain temperature with increasing temperature to obtain the absolute humidity output signal S5. Therefore, an absolute humidity meter that can be used also as a relative humidity meter can be obtained.

Still further, no temperature-compensating humidity sensor is necessary. Therefore, an absolute humidity meter that is less affected by temperature variations can be obtained.

Still further, the humidity sensor 1 changes an impedance Zs thereof exponentially with respect to the relative humidity, and the z-f converting circuit 2 generates the pulse signal S1 whose frequency corresponds to the impedance Zs of the humidity sensor 1. Therefore, the frequency of the pulse signal S1 changes to a large extent. In addition, the signals are processed digitally, which in turn facilitates signal processing and therefore allows an inexpensive absolute humidity meter to be obtained.

In a preferred embodiment, the humidity sensor 1, the z-f converting circuit 2, the time constant control differentiating circuit 3, the waveform shaping circuit 4, and the integrating circuit 5 are contained in a not shown single case. Therefore, an absolute humidity meter that is not only downsized but also less affected by temperature variations because the humidity sensor 1 and the integrating circuit 5 are disposed under the closest degree of same temperature conditions that can be obtained. These components can be accommodated in a 11×27×6-mm case in this embodiment, so that the embodiment can be applied to a great diversity of electronic devices.

In the preferred embodiment, the first integrating circuit 51 has a resistance dividing circuit 51A and a capacitor 513. The resistance dividing circuit 51A includes a fixed resistor 511 and a variable impedance circuit 512 whose impedance changes with temperature. The variable impedance circuit 512 is constructed of a thermistor. The capacitor 513 is connected in parallel with either the fixed resistor 511 or the thermistor 512, so that the terminal voltage of the capacitor 513 becomes the control voltage Vc. Thus the resistance of the thermistor 512 increases or decreases with increasing temperature, which in turn decreases the divided voltage of the fixed resistor 511 or the divided voltage of the thermistor 512, thereby decreasing the control voltage Vc. As a result, the output voltage Vr of the relative humidity signal S4 can be increased with increasing temperature through the second integrating circuit 52. Although the fixed resistor 511 is shown as a variable resistor in the drawing, the fixed resistor 511 is provided to finely adjust the resistance dividing ratio and therefore serves as the fixed resistor after adjustment.

In the embodiment shown in FIG. 1, specifically, the variable impedance circuit 512 is constructed of a negative temperature coefficient (TC) type thermistor, and the capacitor 513 is connected in parallel with the negative TC type thermistor 512. The resistance of the negative TC type thermistor 512 is decreased with increasing temperature. As a result, the divided voltage of the negative TC type thermistor 512 is decreased with increasing temperature, which in turn decreases the control voltage Vc.

In the preferred embodiment, the second integrating circuit 52 has a resistance dividing circuit 52A and the capacitor 523. The resistance dividing circuit 52A includes the fixed resistance 521 and the thermistor 522. The capacitor 523 is connected in parallel with either the fixed resistor 521 or the thermistor 522, and the terminal voltage of the capacitor 523 becomes the absolute humidity signal S5. Thus the resistance of the thermistor 522 is increased or decreased with increasing temperature, which in turn increases the divided voltage of the thermistor 522 or the divided voltage of the fixed resistor 521. As a result, the output voltage Vr of the relative humidity signal S4 is increased with increasing temperature, thereby allowing the absolute humidity signal S5 to be obtained. Although the fixed resistor 521 is shown as a variable resistor in the drawing, the fixed resistor 521 is provided to finely adjust the resistance dividing ratio and therefore serves as the fixed resistor after adjustment.

In the embodiment shown in FIG. 1, specifically, the thermistor 522 is constructed of a negative TC type thermistor, and the capacitor 523 is connected in parallel with the fixed resistor 521. As a result, the divided voltage of the fixed resistor 521 is increased with increasing temperature, which in turn increases the output voltage Vr of the relative humidity signal S4, thereby providing the absolute humidity signal S5.

Figure 5:
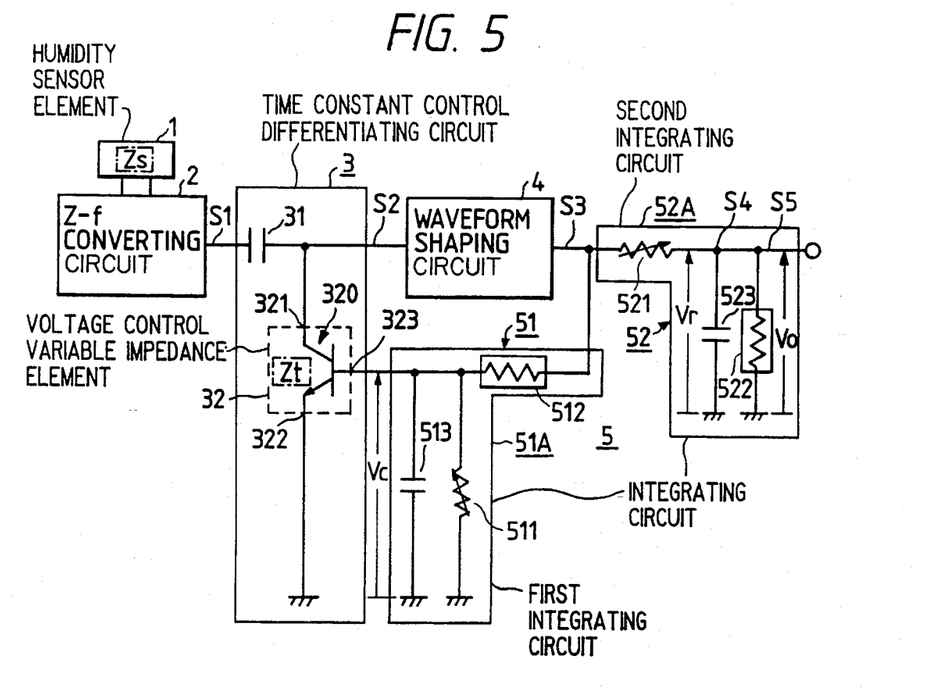
FIG. 5 is a block diagram showing a configuration of an absolute humidity meter, which is another embodiment of the invention.

FIG. 5 is a block diagram showing a configuration of an absolute humidity meter, which is another embodiment of the invention. In FIG. 5, the same reference numerals as those in FIG. 1 denote like parts and components.

In the first integrating circuit 51, the thermistor 512 is constructed of a positive TC type thermistor, and the capacitor 513 is connected in parallel with the fixed resistor 511. The resistance of the positive TC type thermistor 512 is increased with increasing temperature. As a result, when the resistance of the positive TC type thermistor 512 is increased with increasing temperature, the divided voltage of the fixed resistor 511 is decreased, which in turn decreases the control voltage Vc.

In the second integrating circuit 52, the thermistor 522 is constructed of a positive TC type thermistor, and the capacitor 523 is connected in parallel with the positive TC type thermistor 522. As a result, the divided voltage of the positive TC type thermistor 522 is increased with increasing temperature, which in turn increases the output voltage Vr of the relative humidity signal S4, thereby providing the absolute humidity signal S5.

Figure 6:
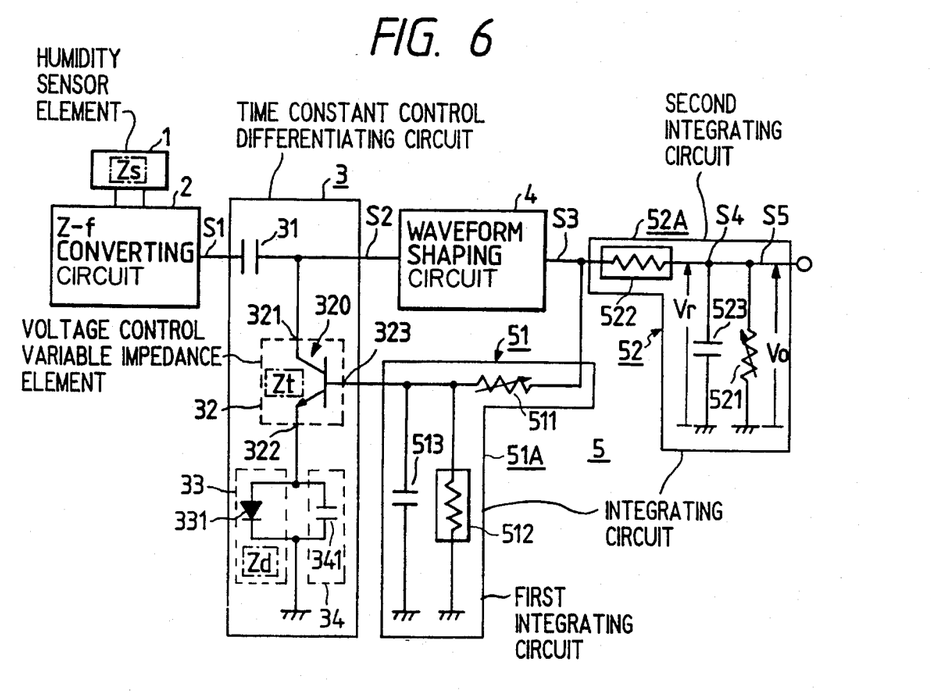
FIG. 6 is a block diagram showing a configuration of an absolute humidity meter, which is still another embodiment of the invention.

FIG. 6 is a block diagram showing a configuration of an absolute humidity meter, which is still another embodiment of the invention. In FIG. 6, the same reference numerals as those in FIG. 1 denote like parts and components.

The time constant control differentiating circuit 3 includes a nonlinear impedance element 33 whose impedance Zd changes exponentially with an applied voltage. The nonlinear impedance element 33 has one terminal thereof connected to the main electrode 322 that is opposite to the main electrode 321 to which the capacitor 31 is connected and the other terminal thereof is grounded. The time constant control differentiating circuit 3 outputs the differentiated signal S2 across both terminals of the voltage control variable impedance element 32 and the nonlinear impedance element 33 which are connected in series with each other. In this embodiment, the differentiated signal S2 whose time constant changes with changing impedance of the voltage control variable impedance element 32 and the nonlinear impedance element 33, and hence whose time constant changes exponentially can be obtained. Thus the nonlinear impedance element 33 supplements linearity that was short when the conventional voltage control variable impedance element 32 corrected the nonlinearity of the humidity sensor 1. As result of this operation, the linearity of the output voltage of the relative humidity signal can be further improved with respect to that of the embodiment shown in FIG. 1, which in turn allows the linearity of the output voltage of the absolute humidity signal to be also further improved.

In a preferred embodiment of the time constant control differentiating circuit 3, the voltage control variable impedance element 32 is constructed of the transistor 320, and the nonlinear impedance element 33 is constructed of a diode 331. A silicon diode, a Schottky barrier diode, or the like may be used as the diode 331. The anode of the diode 331 is connected to the emitter 322 of the transistor 320. The capacitor 31 is connected to the collector 321 of the transistor 320. The control voltage Vc is supplied to the base 323 of the transistor 320. Since the relationship between the base voltage and the emitter current of the transistor 320 is exponential in this embodiment, the impedance Zt of the transistor 320 in operation also changes exponentially according to the control voltage Vc supplied to the base. Since the relationship between the forward voltage and the forward current of the diode 331 is exponential, the impedance Zd of the diode 331 in operation also changes exponentially. As a result, the application of the control voltage Vc degenerates the transistor 320 and the diode 331, thereby improving the linearity of the absolute humidity signal S5.

The time constant control differentiating circuit 3 has an impedance adjusting circuit 34. The impedance adjusting circuit 34 is connected in parallel with the nonlinear impedance element 33. In this embodiment, the impedance adjusting circuit 34 decreases the synthetic impedance when the impedance Zd is corrected to too large a value by the nonlinear impedance element 33, which in turn permits appropriate correction. As a result of this operation, the linearity of the absolute humidity signal S5 can be further improved.

In an embodiment in which the impedance adjusting circuit 34 is constructed of a capacitor, the impedance zd of the nonlinear impedance element 33 can be adjusted in accordance with the frequency of the z-f converting circuit.

In an embodiment in which the impedance adjusting circuit 34 is constructed of a resistor (not shown), the impedance Zd of the nonlinear impedance element 33 can be adjusted independently of the frequency.

In an embodiment in which the impedance adjusting circuit 34 is constructed of diodes (not shown), the impedance Zd of the nonlinear impedance element 33 can be adjusted to a value equal to the reciprocal of an integer that is the number of diodes connected.

Figure 7:
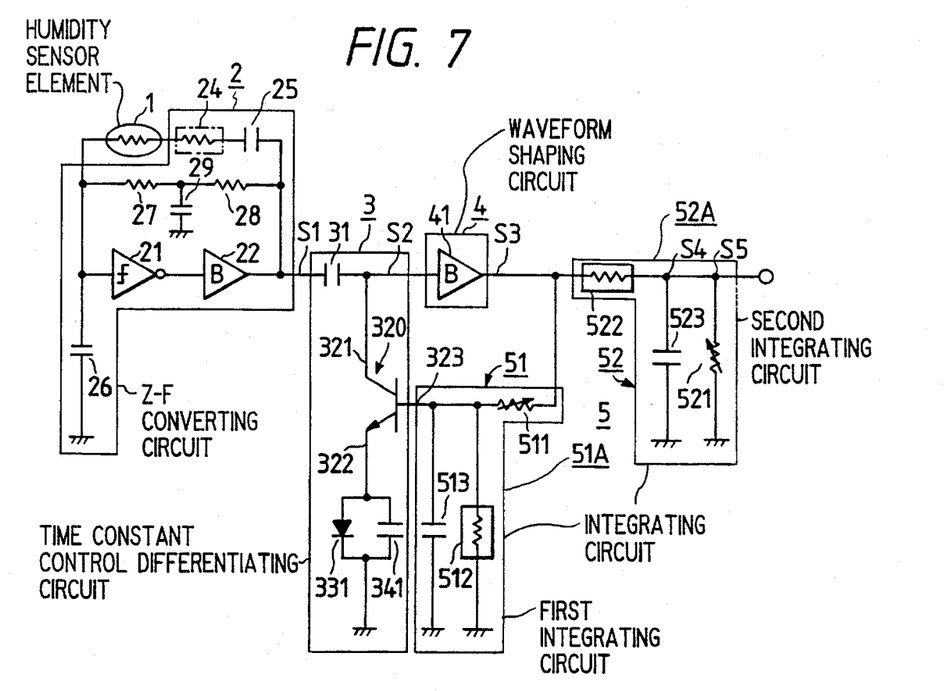
FIG. 7 is a specific circuit diagram of the absolute humidity meter of the invention.

FIG. 7 is a specific circuit diagram of the absolute humidity meter of the invention. In FIG. 7, the same reference numerals as those in FIGS. 1, 5, and 6 denote like parts and components.

The z-f converting circuit 2 has a Schmitt trigger 21, a buffer 22, a resistor 23, a thermistor 24, a capacitor 25, and a capacitor 26. The humidity sensor 1, the thermistor 24, and the capacitor 25 are connected in series with one another; one terminal of the humidity sensor 1, which is one terminal of the series circuit, is connected to the input terminal of the Schmitt trigger 21; and one terminal of the capacitor 25, which is the other terminal of the series circuit, is connected to the output terminal of the buffer 22. The Schmitt trigger 21 and the buffer 22 are constructed of ICs such as CMOSs and TTLs. The thermistor 24 compensates for changes due to temperature variations in the impedance Zs of the humidity sensor 1. The capacitor 25 blocks the flow of direct current. The buffer 22 decreases the output impedance of the Schmitt trigger 21 and shapes waveforms. One terminal of the resistor 23 is connected to the input terminal of the Schmitt trigger 21 and the other terminal thereof is connected to the output terminal of the buffer 22. One terminal of the capacitor 26 is connected to the input terminal of the Schmitt trigger 21. As a result of this configuration, the z-f converting circuit 2 is oscillated by the relationship between the impedances of the humidity sensor 1, the resistor 23, the thermistor 24 and the impedance of the capacitor 26, and outputs the pulse signal S1 whose frequency changes with changing impedance of the humidity sensor 1.

The waveform shaping circuit 4 is constructed of a buffer 41. An IC such as a CMOS or a TTL is used as the buffer 41. The buffer 41 binary-valued the differentiated signal S2 with a threshold level as a predetermined voltage, and outputs the pulse signal train S3.

Figure 8:
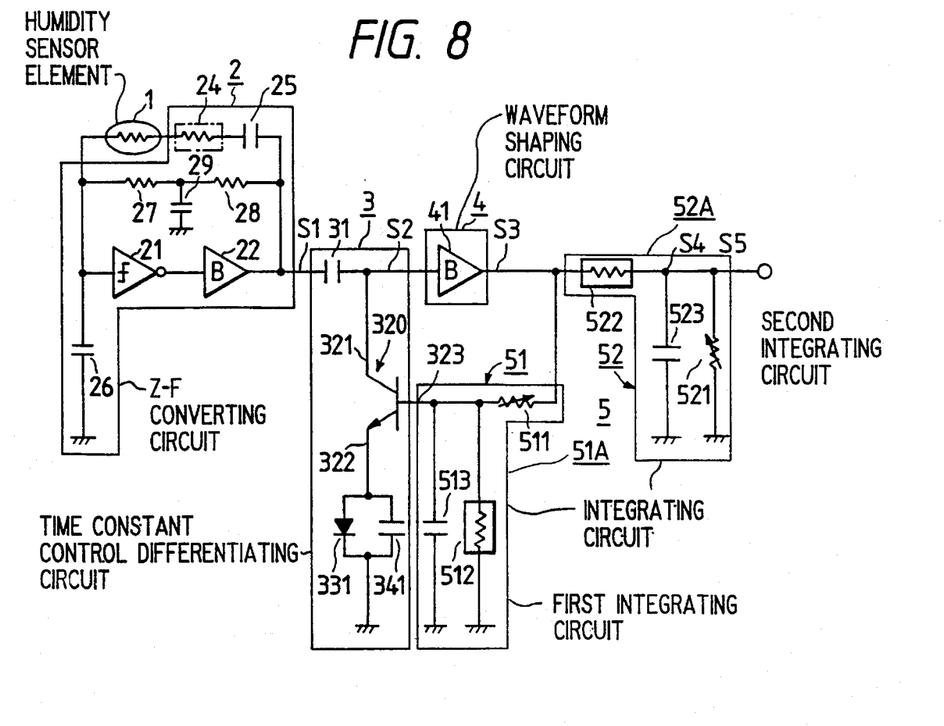
FIG. 8 is another specific circuit diagram of the absolute humidity meter of the invention.

FIG. 8 is another specific circuit diagram of the absolute humidity meter of the invention. In FIG. 8, the same reference numerals as those in FIG. 7 denote like parts and components. A resistor 27 is connected in series with a resistor 28, and both terminals of the series circuit are connected to the input terminal of the Schmitt trigger 21 and to the output terminal of the buffer 22, respectively. A capacitor 29 has one terminal thereof connected to a node of the series connection between the resistor 27 and the resistor 28 and the other terminal thereof grounded. According to this configuration, ac component contained in a pulse signal is bypassed by the capacitor 29, so that the impedance across both terminals of the series circuit constructed of the resistor 27 and the resistor 28 can be maintained at a high level. This prevents the synthetic impedance of the series circuit, which is constructed of the resistor 27 and the resistor 28, connected in parallel with the humidity sensor 1 from decreasing, which in turn allows the z-f converting circuit 2 to convert a change in the resistance of the humidity sensor 1 into a pulse signal S1 efficiently.

Figure 9:
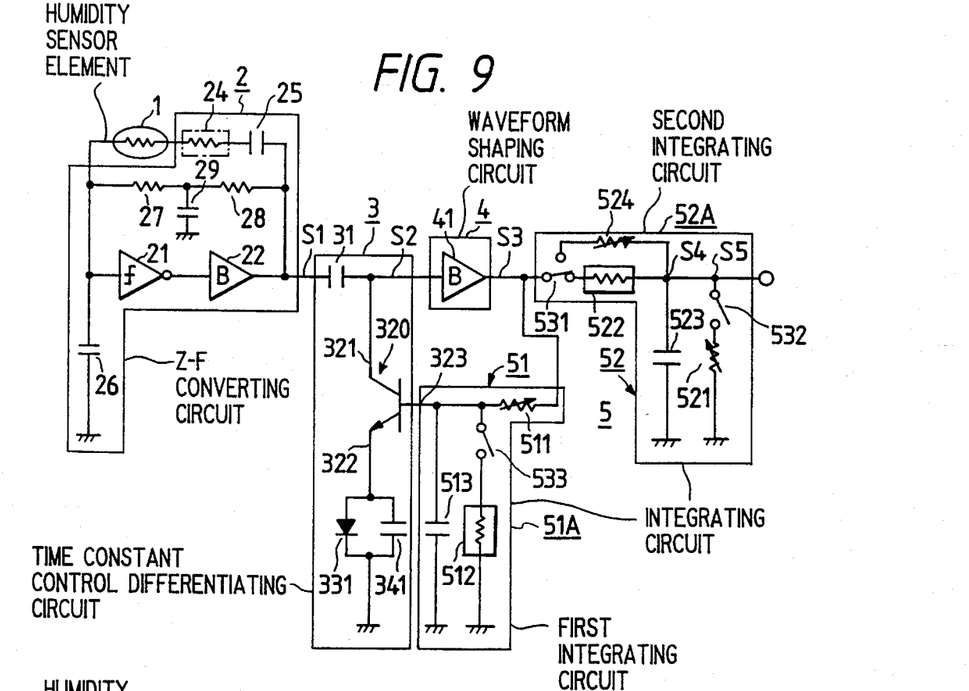
FIG. 9 is still another specific circuit diagram of the absolute humidity meter of the invention.

FIG. 9 is still another specific circuit diagram of the absolute humidity meter of the invention. This circuit is designed in consideration of using the humidity meter both as a relative humidity meter and as an absolute humidity meter. In FIG. 9, the same reference numerals as those in FIG. 8 denote like parts and components. A switch 531 is connected to a fixed resistor 524 when the meter is used as the relative humidity meter, while the switch 531 is connected to the thermistor 522 when the meter is used as the absolute humidity meter. Switches 532 and 533 are opened when the meter is used as the relative humidity meter, while the switches 532 and 533 are closed when the meter is used as the absolute humidity meter. As a result of this configuration, the meter can be used either as the relative humidity meter or the absolute humidity meter only by the switching the switches 531 to 533. Each of the switches 531 to 533 may be constructed of a selector switch, an analog multiplexer, or the like.

Figure 10:
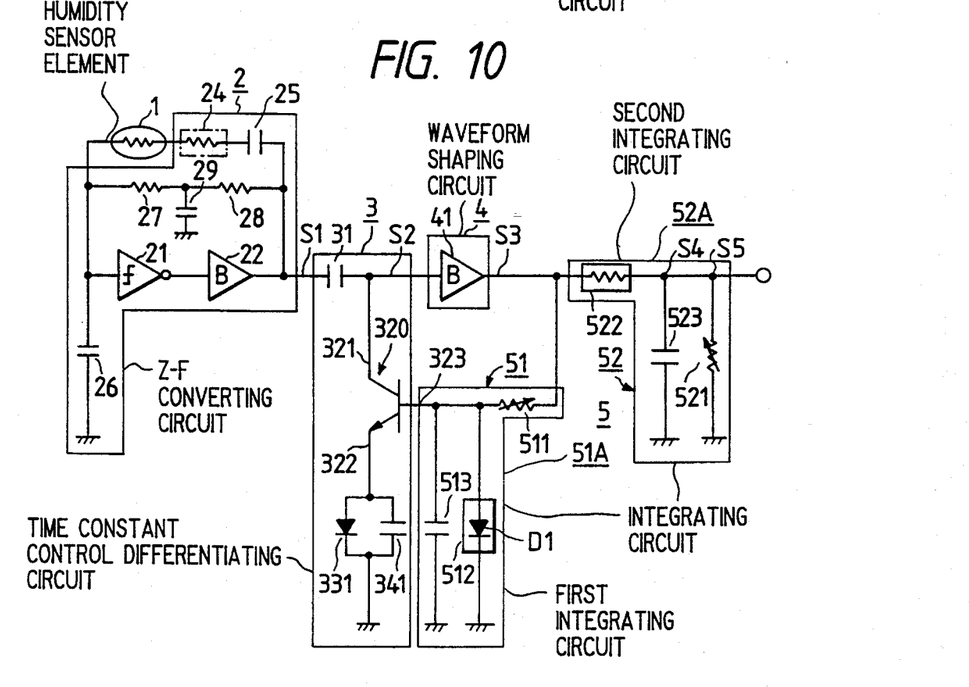
FIG. 10 is still another specific circuit diagram of the absolute humidity meter of the invention.

FIG. 10 is still another specific circuit diagram of the absolute humidity meter of the invention. In FIG. 10, the same reference numerals as those in FIGS. 1, 6, and 8 denote like parts and components. The variable impedance circuit 512 is constructed of a diode D1. Since the impedance of the diode D1 in operation decreases with increasing temperature, the divided voltage of the diode D1 decreases, which in turn decreases the control voltage Vc.

Figure 11:
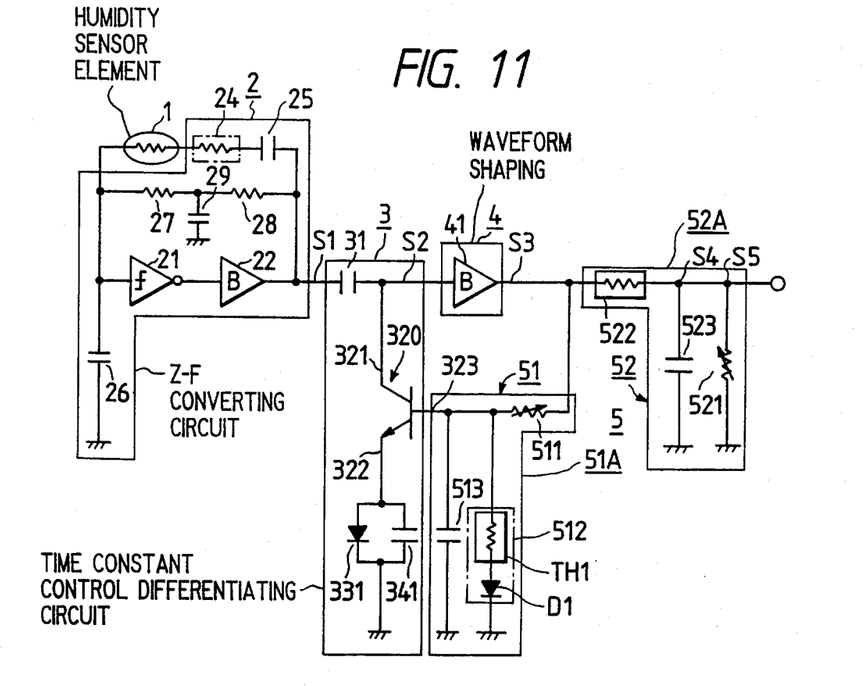
FIG. 11 is still another specific circuit diagram of the absolute humidity meter of the invention.

FIG. 11 is still another specific circuit diagram of the absolute humidity meter of the invention. In FIG. 11, the same reference numerals as those in FIGS. 1, 6, and 8 denote like parts and components. The variable impedance circuit 512 is constructed of a series circuit consisting of a negative TC type thermistor TH1 and the diode D1. Since the impedance of the negative TC type thermistor TH1 and the diode D1 in operation decreases with increasing temperature, the divided voltage of the negative TC type thermistor TH1 and the diode D1 decreases, which in turn decreases the control voltage Vc.

Figure 12:
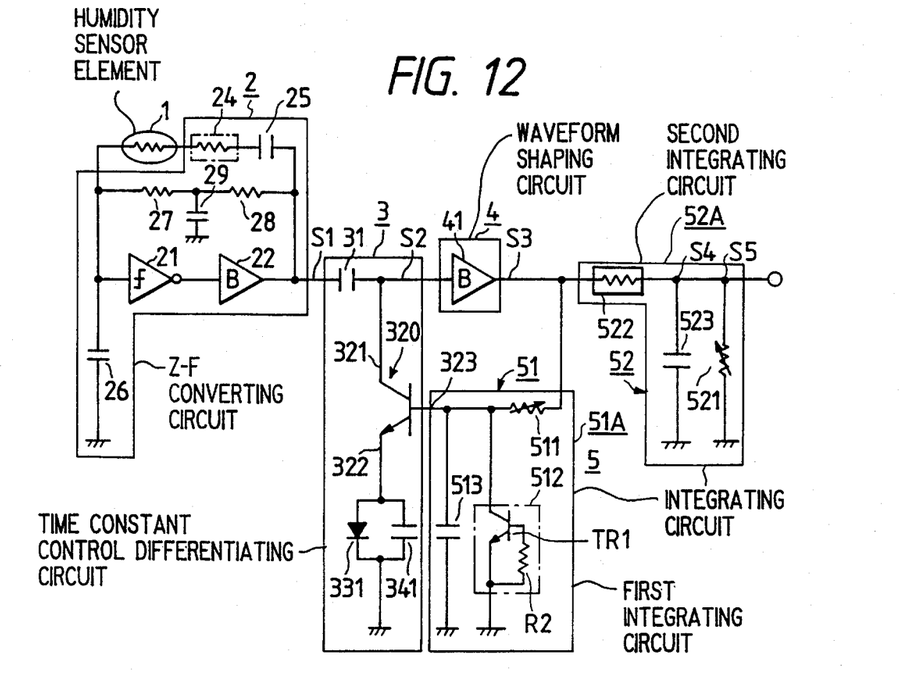
FIG. 12 is still another specific circuit diagram of the absolute humidity meter of the invention.

FIG. 12 is still another specific circuit diagram of the absolute humidity meter of the invention. In FIG. 12, the same reference numerals as those in FIGS. 1, 6, and 8 denote like parts and components. The variable impedance circuit 512 includes a transistor TR1 and a fixed resistor R2. The collector of the transistor TR1 is connected to the fixed resistor 511 and the emitter thereof is grounded. One terminal of the fixed resistor R2 is connected to the base of the transistor TR1 and the other terminal thereof is grounded. The capacitor 513 is connected in parallel with the collector and the emitter of the transistor TR1. Since the impedance of the transistor TR1 in operation decreases with increasing temperature, the divided voltage of the transistor TR1 decreases, which in turn decreases the control voltage Vc.

Figure 13:
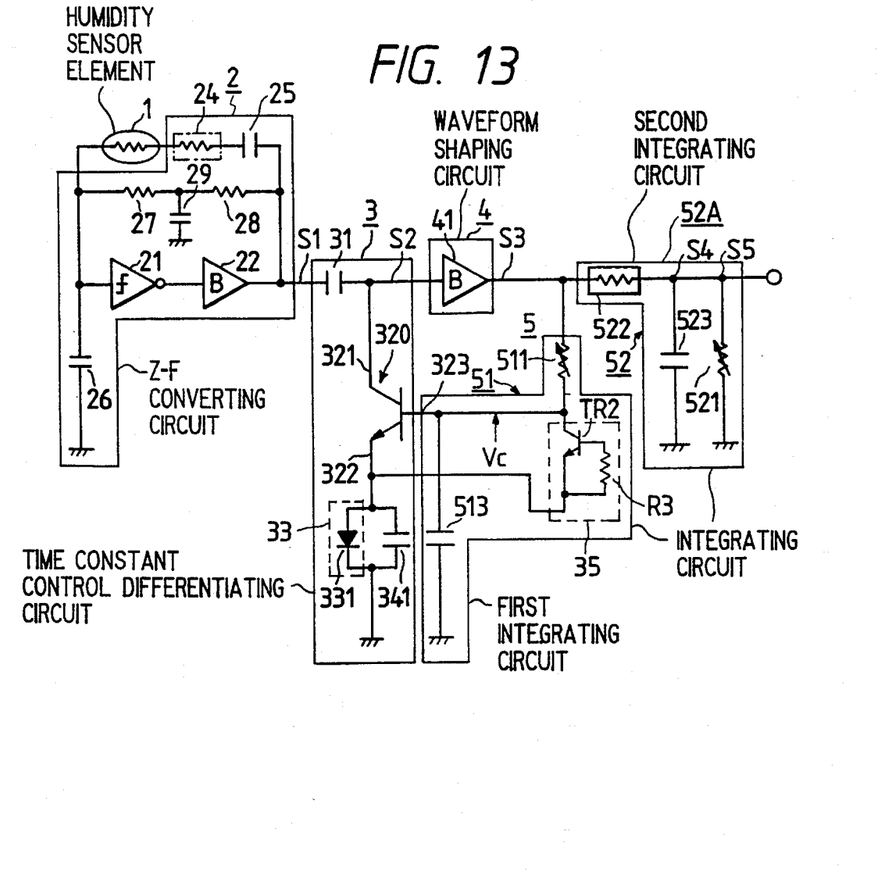
FIG. 13 is still another specific circuit diagram of the absolute humidity meter of the invention.

FIG. 13 is still another specific circuit diagram of the absolute humidity meter of the invention. In FIG. 13, the same reference numerals as those in FIGS. 1, 6, and 8 denote like parts and components. The time constant control differentiating circuit 3 has a control voltage adjusting circuit 35. The control voltage adjusting circuit 35 biases the nonlinear impedance element 33 in accordance with the control voltage Vc obtained by integration at the first integrating circuit 51. Specifically, the control voltage adjusting circuit 35 includes a transistor TR2 and a fixed resistor R3. The nonlinear impedance element 33 is constructed of a diode 331. The collector of the transistor TR2 is connected to the capacitor 513 constituting the first integrating circuit 51 and the emitter thereof is connected to the diode 331. The fixed resistor R3 is connected to the emitter and the base of the transistor TR2. In this embodiment, the diode 331 is biased by the current flowing through the transistor TR2, and the potential of the anode of the diode 331, i.e., the potential of the emitter 322 of the transistor 320 increases, which is substantially equivalent to a decrease in the divided voltage when the resistance dividing circuit 51A (see FIG. 8) is arranged in the first integrating circuit 51. Therefore, this embodiment is characterized as providing a wide adjustment range for a variety of types of humidity sensors.

Figure 14:
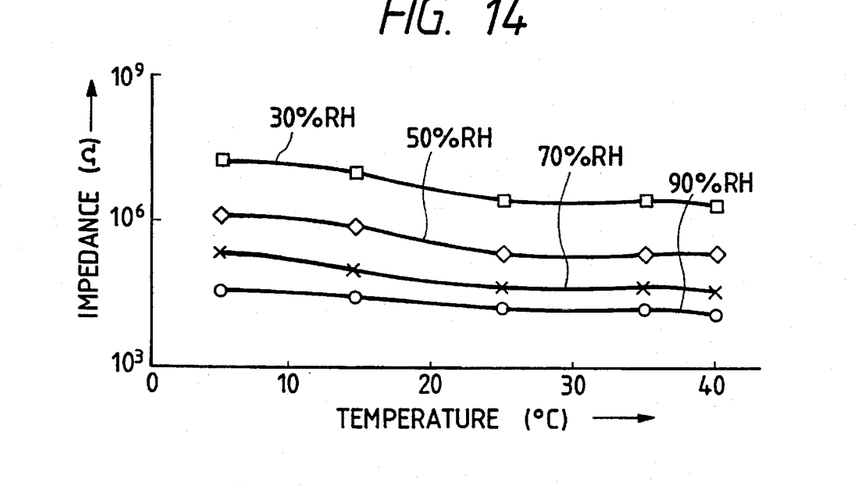
FIG. 14 is a diagram showing changes in the impedance of another humidity sensor.

FIG. 14 is a diagram showing changes in the impedance of another humidity sensor. The same reference numerals as those in FIG. 2 denote like factors. The humidity sensor shown in FIG. 14 exhibits a small resistance changing rate with respect to the relative temperature compared with the humidity sensor shown in FIG. 2. The resistance changing rate with respect to the relative humidity is also decreased. As a result, in the aforementioned circuit configurations, the output voltage may be decreased where the relative humidity is high, which may in turn reduce the linearity of the output voltage with respect to the absolute humidity.

Figure 15:
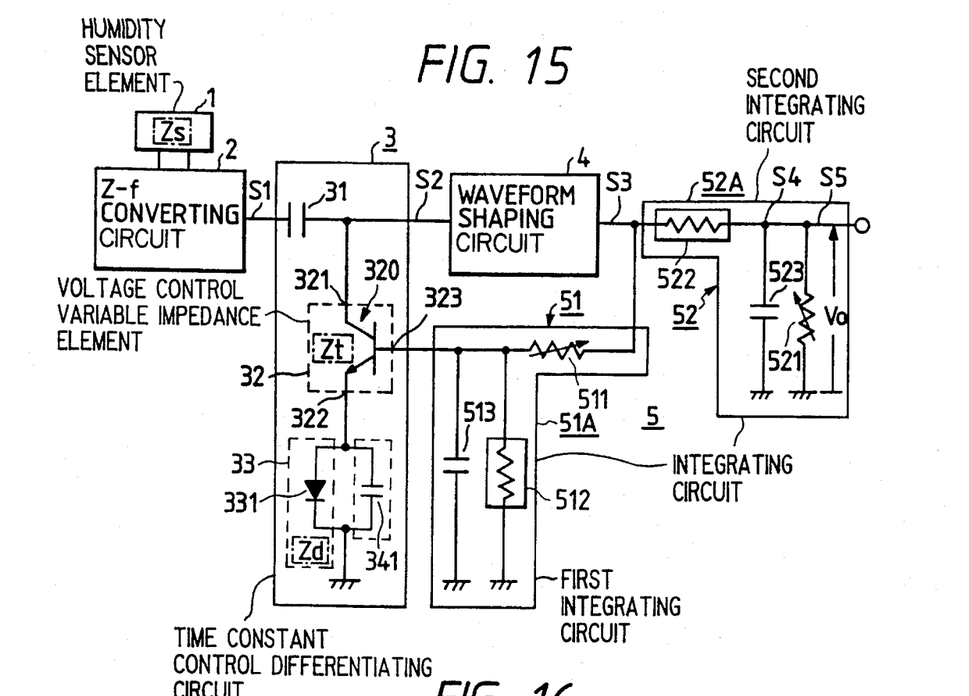
FIG. 15 is still another specific circuit diagram of the absolute humidity meter of the invention.
Figure 16:
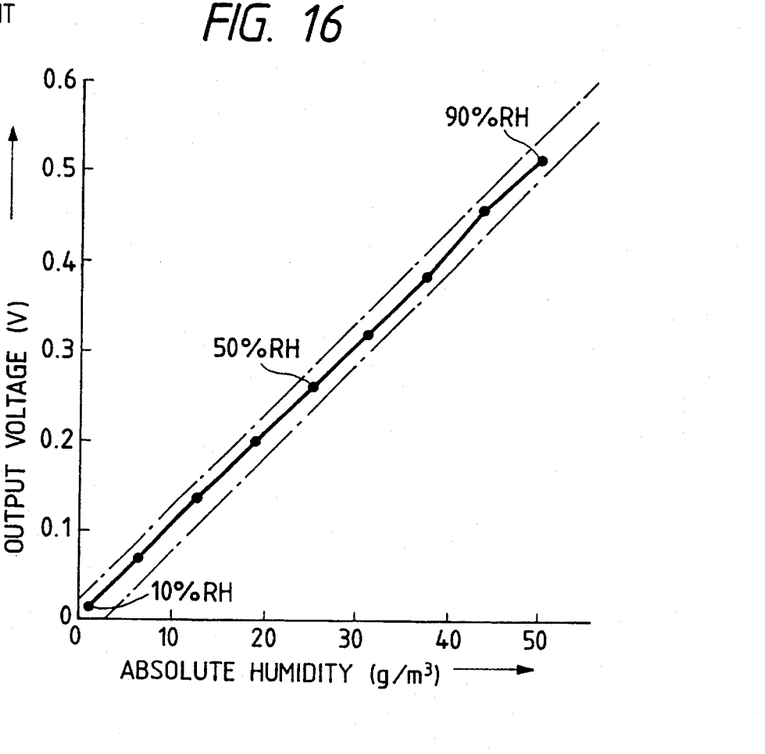
FIG. 16 is a diagram showing a relationship between the absolute humidity and the output voltage when the circuit shown in FIG. 15 is used.

FIG. 15 is still another specific circuit diagram of the absolute humidity meter of the invention, and FIG. 16 is a diagram showing a relationship between the absolute humidity and the output voltage in the case of using the circuit shown in FIG. 15. FIG. 16 shows a case where the ambient temperature is 45° C. The range indicated by the one dot chain lines is a ±2 (g/m$^3$) error range. In FIG. 15, the same reference numerals as those in FIGS. 1, 6, and 8 denote like parts and components. A humidity sensor denoted by reference numeral 1 is constructed of the humidity sensor shown in FIG. 14. The voltage control variable impedance element 320 includes two transistors, which are Darlington-connected. According to this configuration, the impedance Zt of the voltage control variable impedance 320 changes to a large extent even with small changes in the control voltage Vc. As a result, the linearity of the output voltage is increased where the relative humidity is high as shown in FIG. 16 even if a humidity sensor whose resistance changing rate with respect to the relative humidity is small. Although not shown in the drawing, such a high linearity as to be within the range indicated by the one dot chain lines (see FIG. 16) can be obtained even at ambient temperatures of 5°, 15°, 25°, 35° C. This allows a humidity sensor with a small resistance changing rate can also be used, which can in turn provide an absolute humidity meter to which a variety of types of humidity sensors can be applied.

As described in the foregoing, the invention can provide the following advantages.

An absolute humidity meter that is not based on the heat dissipation coefficient of a thermistor can be provided.

An absolute humidity meter that is less affected by variations between a plurality of detecting elements and location temperature differences can be provided while using only one detecting element.

An absolute humidity meter that can be used also as a relative humidity meter can be provided by using a detecting element whose impedance changes with relative humidity.

An absolute humidity meter that is less affected by temperature variations can be provided.

An absolute humidity meter that facilitates signal processing and that can be manufactured inexpensively can be provided.

An absolute humidity meter to which a variety of types of humidity sensors are applicable can be provided.

What is claimed is:

1. An absolute humidity meter comprising:

a humidity sensor having an electrical impedance changing exponentially with respect to a relative humidity;

an impedance-frequency converting circuit for generating a pulse signal whose frequency corresponds to the impedance of said humidity sensor;

a time constant control differentiating circuit including a capacitor and a voltage control variable impedance element connected in series with each other, said voltage control variable impedance element including a three-terminal element having main electrodes and a control electrode, an impedance of said voltage control variable impedance element changing exponentially in accordance with a voltage applied to the control electrode, a differentiated signal being obtained by differentiating the pulse signal being outputted across both terminals of the main electrodes;

a waveform shaping circuit coupled with output of said time constant controlled differentiating circuit, for generating a pulse signal when the differentiated signal exceeds a predetermined threshold level; and an integrator including a first integrating circuit and a second integrating circuit, said first integrating circuit coupled with output of said waveform shaping circuit for integrating the inputted pulse signal train and supplying a voltage obtained by the integration to the control electrode of the voltage control variable impedance element, and said second integrating circuit coupled with the output of said waveform shaping circuit for integrating the pulse signal train and outputting a voltage obtained by the integration which represents a relative humidity signal, wherein at least one of the first integrating circuit and the second integrating circuit includes a thermal sensing element placed in close association to the humidity sensor so as to monitor temperature and change in temperature at a location of said humidity sensor to control one of the control voltage and the output voltage of the relative humidity signal in accordance with changes in the temperature of the humidity sensor to obtain an absolute humidity signal.

2. An absolute humidity meter according to claim 1, wherein said humidity sensor, said impedance-frequency converting circuit, said time constant control differentiating circuit, said waveform shaping circuit, and said integrating circuit are contained in a single case.

3. An absolute humidity meter according to claim 1, wherein the first integrating circuit has a resistance dividing circuit and a capacitor, the resistance dividing circuit including a fixed resistor and a variable impedance circuit whose impedance changes with temperature, the capacitor being connected in parallel with one of the fixed resistor and the variable impedance circuit, a terminal voltage of the capacitor being applied to the control electrode of said voltage control variable impedance element as the control voltage.

4. An absolute humidity meter according to claim 3, wherein the variable impedance circuit includes at least one of a negative temperature coefficient (TC) type thermistor, a diode, a transistor, and a positive TC type thermistor.

5. An absolute humidity meter according to claim 1, wherein the second integrating circuit has a resistance dividing circuit and a capacitor, the resistance dividing circuit including a fixed resistor and a thermistor, the capacitor being connected in parallel with one of the fixed resistor and the thermistor, a terminal voltage of the capacitor becoming an output voltage of the absolute humidity signal.

6. An absolute humidity meter according to claim 5, wherein the thermistor is constructed by one of a negative TC type thermistor or a positive TC type thermistor.

7. An absolute humidity meter according to claim 1, wherein the voltage control variable impedance element includes a transistor, a collector and an emitter of the transistor constituting the main electrodes, a base thereof constituting the control electrode.

8. An absolute humidity meter according to claim 7, wherein the voltage control variable impedance element includes two transistors which are Darlington-connected.

9. An absolute humidity meter according to claim 1, wherein the time constant control differentiating circuit includes a nonlinear impedance element whose impedance changes exponentially with an applied voltage, the nonlinear impedance element being connected to the main electrode opposite to the main electrode to which the capacitor is connected, the time constant control differentiating circuit outputting the differentiated signal across both terminals of the voltage control variable impedance element and the nonlinear impedance element connected in series with each other.

10. An absolute humidity meter according to claim 9, wherein said nonlinear impedance element is constructed of a diode, an anode of the diode being connected to the main electrode opposite to the main electrode to which the capacitor is connected.

11. An absolute humidity meter according to claim 9, wherein the time constant control differentiating circuit has an impedance adjusting circuit, the impedance adjusting circuit being connected in parallel with the nonlinear impedance element.

12. An absolute humidity meter according to claim 11, wherein the impedance adjusting circuit is constructed of a capacitor.

13. An absolute humidity meter according to claim 10, wherein the time constant control differentiating circuit has an impedance adjusting circuit, the impedance adjusting circuit being connected in parallel with the nonlinear impedance element.

14. An absolute humidity meter according to claim 13, wherein the impedance adjusting circuit is constructed of a capacitor.

15. An absolute humidity meter according to claim 10, wherein the time constant control differentiating circuit has a control voltage adjusting circuit, the control voltage adjusting circuit biasing the nonlinear impedance element in accordance with the voltage obtained by the integration at the first integrating circuit.

16. An absolute humidity meter according to claim 15, wherein the control voltage adjusting circuit includes a transistor and a fixed resistor, a collector of the transistor being connected to the capacitor of the first integrating circuit, an emitter thereof being connected to the nonlinear impedance element, the fixed resistor being connected to the emitter and a base of the transistor.

* * * * *